(12) United States Patent
Chen et al.

(10) Patent No.: US 9,726,012 B2
(45) Date of Patent: Aug. 8, 2017

(54) SYSTEMS AND METHODS FOR OPTICAL FLUID IDENTIFICATION APPROXIMATION AND CALIBRATION

(71) Applicant: Halliburton Energy Services, Inc., Houston, TX (US)

(72) Inventors: Dingding Chen, Tomball, TX (US); David Perkins, The Woodlands, TX (US); Jing Cynthia Shen, Houston, TX (US); Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 204 days.

(21) Appl. No.: 14/240,611

(22) PCT Filed: Mar. 8, 2013

(86) PCT No.: PCT/US2013/029861
§ 371 (c)(1),
(2) Date: Feb. 24, 2014

(87) PCT Pub. No.: WO2014/137354
PCT Pub. Date: Sep. 12, 2014

(65) Prior Publication Data
US 2016/0032719 A1    Feb. 4, 2016

(51) Int. Cl.
*E21B 49/08* (2006.01)
*G01N 21/27* (2006.01)
(Continued)

(52) U.S. Cl.
CPC ........... *E21B 49/08* (2013.01); *G01N 21/274* (2013.01); *G01N 21/31* (2013.01); *G01N 21/84* (2013.01);
(Continued)

(58) Field of Classification Search
CPC ....... E21B 49/08; G01N 21/84; G01N 21/274
See application file for complete search history.

(56) References Cited

U.S. PATENT DOCUMENTS 4,629,702 A    12/1986 Fan
6,441,388 B1 *  8/2002 Thomas ............. A61B 5/14532
                                                250/339.09
(Continued)

FOREIGN PATENT DOCUMENTS

WO         92/07326 A1    4/1992
WO         01/84122 A2   11/2001
WO    2009/082418 A2     7/2009

OTHER PUBLICATIONS

International Preliminary Report on Patentability issued in related PCT Application No. PCT/US2013/029861, mailed Sep. 17, 2015 (7 pages).
(Continued)

*Primary Examiner* — Manuel Rivera Vargas
(74) *Attorney, Agent, or Firm* — Benjamin Fite; Baker Botts L.L.P.

(57) ABSTRACT

Systems and methods for optical fluid identification approximation and calibration are described herein. One example method includes populating a database with a calculated pseudo optical sensor (CPOS) response of a first optical tool to a first sample fluid. The CPOS response of the first optical tool may be based on a transmittance spectrum of a sample fluid and may comprise a complex calculation using selected components of the first optical tool. A first model may be generated based, at least in part, on the database. The first model may receive as an input an optical sensor response and output a predicted fluid property. A second model may also be generated based, at least in part, on the database. The second model may receive as an input at least one known/measured fluid/environmental property value and may output a predicted pseudo optical sensor response of the first optical tool.

16 Claims, 9 Drawing Sheets

(51) Int. Cl.
  *G01N 21/31*   (2006.01)
  *G01N 21/84*   (2006.01)
  *G01N 33/28*   (2006.01)
  *G01N 21/3577*   (2014.01)

(52) U.S. Cl.
  CPC ..... *G01N 21/3577* (2013.01); *G01N 33/2823* (2013.01); *G01N 2201/1296* (2013.01)

(56) References Cited

U.S. PATENT DOCUMENTS

| | | |
|---|---|---|
| 7,500,517 B2 | 3/2009 | Looney et al. |
| 2010/0155078 A1 | 6/2010 | Walters et al. |
| 2010/0212904 A1 | 8/2010 | Billman |

OTHER PUBLICATIONS

International Search Report and Written Opinion issued in related International Application No. PCT/US2013/029861, mailed Nov. 5, 2013, 11 pages.

Kompany-Zareh, Mohsen et al., "Multi-Way Based Calibration Transfer Between Two Raman Spectrometers", The Analsyt (vol. 135, No. 6. Jun. 2010), pp. 1382-1388.

Fuedale, R.N., et al., "Transfer of Multivariate Calibration Models: A Review", Chemotronics and Intelligent Laboratory Systems, Elsevier Science Publishers B.V., Amsterdam, NL (vol. 64, No. 2. Nov. 28, 2002), pp. 181-192.

\* cited by examiner

SYSTEMS AND METHODS FOR OPTICAL FLUID IDENTIFICATION APPROXIMATION AND CALIBRATION

CROSS-REFERENCE TO RELATED APPLICATION

This application is a U.S. National Stage Application of International Application No. PCT/US2013/029861 filed Mar. 8, 2013, and which is hereby incorporated by reference in its entirety.

BACKGROUND

The present disclosure relates generally to downhole measurement and logging techniques for subterranean drilling operations and, more particularly, to systems and methods for optical fluid identification ("ID") approximation and calibration.

Downhole fluid identification using predictive models calibrated with sensor responses is typical in downhole measurement and logging operations. In most instances, measurements from the downhole tool must be calibrated with measurements from a laboratory tool, meaning that measurements on the two tools need to be taken on the same samples under the same testing conditions. In many instances, however, matching the samples and testing conditions is difficult due to variations between sample properties from different sources, measurement inconsistencies, the availability of required fluids at different times and locations, and the lack of a standard procedure during the early phases of system implementation.

FIGURES

Some specific exemplary embodiments of the disclosure may be understood by referring, in part, to the following description and the accompanying drawings.

FIG. 1 illustrates an example functional flow diagram, according to aspects of the present disclosure.

FIGS. 2A-H illustrate example spectra, values, and outputs for processing algorithms described herein, according to aspects of the present disclosure.

Figure 1:
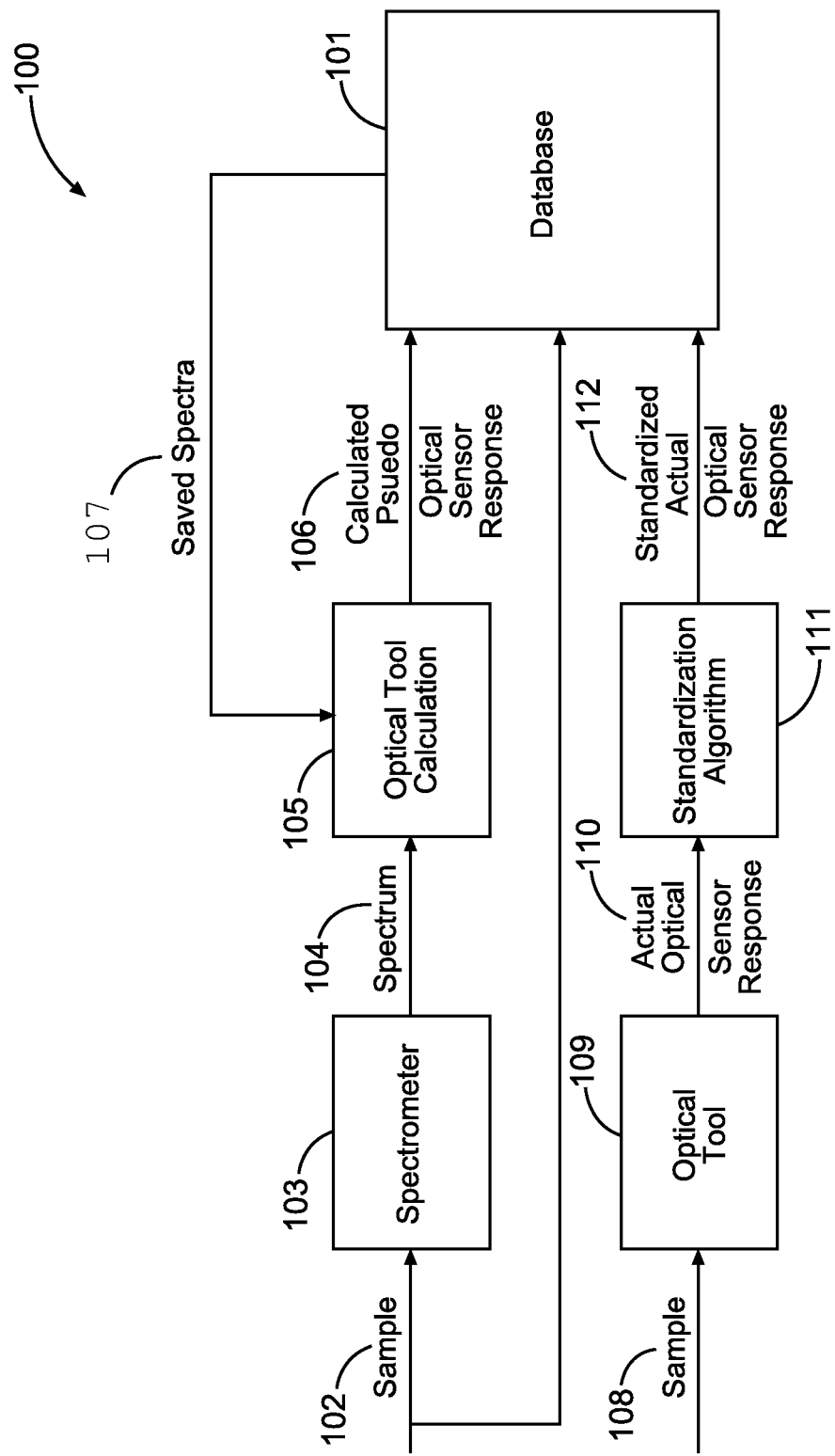

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to downhole measurement and logging techniques for subterranean drilling operations and, more particularly, to systems and methods for optical fluid ID approximation and calibration.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the well below), or otherwise nonlinear wellbores in any type of subterranean formation. Embodiments may be applicable to injection wells, and production wells, including natural resource production wells such as hydrogen sulfide, hydrocarbons or geothermal wells; as well as borehole construction for river crossing tunneling and other such tunneling boreholes for near surface construction purposes or borehole u-tube pipelines used for the transportation of fluids such as hydrocarbons. Embodiments described below with respect to one implementation are not intended to be limiting.

According to aspects of the present disclosure, systems and methods for optical fluid identification approximation and calibration are described herein. One example method includes populating a database with a calculated pseudo optical sensor (CPOS) response of a first optical tool to a first sample fluid. The first optical tool may be an abstract optical tool, and the CPOS response of the abstract optical tool may be based on a transmittance spectrum of a sample fluid and may comprise a complex calculation using selected components of the abstract optical tool. The output of the calculation, and at least one characteristic of the first sample fluid, may be stored in the database. A first model may be generated based, at least in part, on the database. The first model may comprise an optical fluid ID prediction model, and may receive as an input an optical sensor response and output a predicted fluid property. Although the first model may be generated based on the known samples stored in the database, it may be used to identify properties of unknown samples as well. In certain embodiments, a second model may also be generated based, at least in part, on the database. The second model may comprise an optical sensor response model, and may receive as an input at least one known/measured fluid/environmental property value and output a predicted pseudo optical sensor (PPOS) response of the first optical tool, which may differ from the CPOS response in that it is not calculated directly using laboratory data. As will be described below, the two models and the populated database may be leveraged to increase the robustness of optical fluid IDs, as well as increase the flexibility of calibration between the laboratory environment and actual optical tools used within a downhole environment.

FIG. 1 shows an example functional flow diagram 100 for populating a database 101, according to aspects of the present disclosure. As can be seen, a sample fluid 102 may be input into a measurement tool, such as a spectrometer 103. Certain characteristics of the fluid, such as chemical concentrations, density, etc. may be stored directly into database 101. The spectrometer 103 may output an optical spectrum 104 corresponding to the sample fluid 102. The optical spectrum 104 may then be used in an optical tool calculation 105 to determine a CPOS response 106 of an optical tool, which may be an abstract optical tool with a selected optical tool configuration, including an optical tool configuration that corresponds to an actual optical tool that will be deployed downhole. In certain embodiments, the CPOS response 106 may be a transmittance of the sample fluid 102, and may be determined by solving equation (1).

$$OS(i)=((TrsIR \bullet *I_o \bullet *SapIR) \times NBF(i))/((TrsIR \bullet *I_o \bullet *SapIR) \times NDF) \quad (1)$$

In equation (1), •* is an element-by-element multiplication operator; x is a matrix multiplication operator; OS(i) comprises an optical sensor response; TrsIR comprises a measured transmittance spectroscopy of the sample fluid; $I_o$ comprises a light intensity of the optical tool; SapIR comprises a sapphire window transmittance of the optical tool; NBF(i) comprises a plurality of narrow band filters; and NDF comprises a broad band neutral density filter. Notably, equation (1) may generate a "pseudo" optical sensor response—an optical sensor response representation of an abstract optical tool to a particular fluid, rather than the actual response of an actual optical tool. The pseudo optical sensor response generated by equation (1) is characterized as "calculated" (CPOS) because it is calculated from laboratory representations of optical tools configurations. PPOS responses, in contrast, and as will be described below, may be output from a model generated from the database, and are not directly calculated using the laboratory representations of optical tools configurations. In certain embodiments, a general case of a normalized optical response can be defined and calculated using equation (2).

$$OS(i)=(SyS \times FiL(i))/(SyS \times NDF) \quad (2)$$

In equation (2), OS(i) comprises an optical sensor response; SyS comprises an optical system transmittance function; FiL(i) comprises a plurality of optical filters; and NDF comprises a broad band neutral density filter.

Although the equations above describe the use of transmittance values, including TrsIR and SapIR and SyS, and may output transmittance values in the CPOS and PPOS, the methods and systems described herein are not limited to determining transmittance values. Rather, other optical characteristics are possible, such as absorbance, reflectance, and diffuse reflectance, and the equations described here, including equations (1) and (2) may be modified accordingly. For example, rather than transmittance spectra TrsIR and SapIR, their absorbance, reflectance, and diffuse reflectance spectra equivalents may be used instead. Some of the variables in the equations may also be interchanged with well known testing and computational values. For example, the narrow band filters in equation (1) may be interchanged with an Integrated Computational Element (ICE). Exemplary ICEs may comprise optical computing devices with various filter elements that derive data from light signals by weighing frequency components of the light signals. As will be appreciated, variations of the structural components of the optical computing devices described may be suitable, without departing from the scope of the disclosure, and therefore should not be considered limiting to the various embodiments disclosed herein.

Figure 2A:
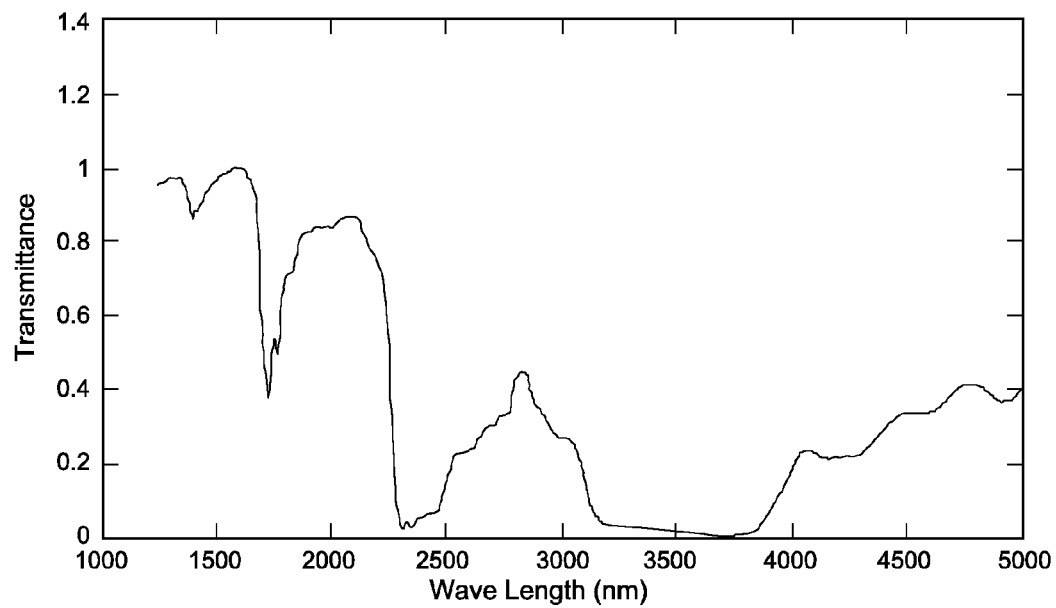
Figure 2B:
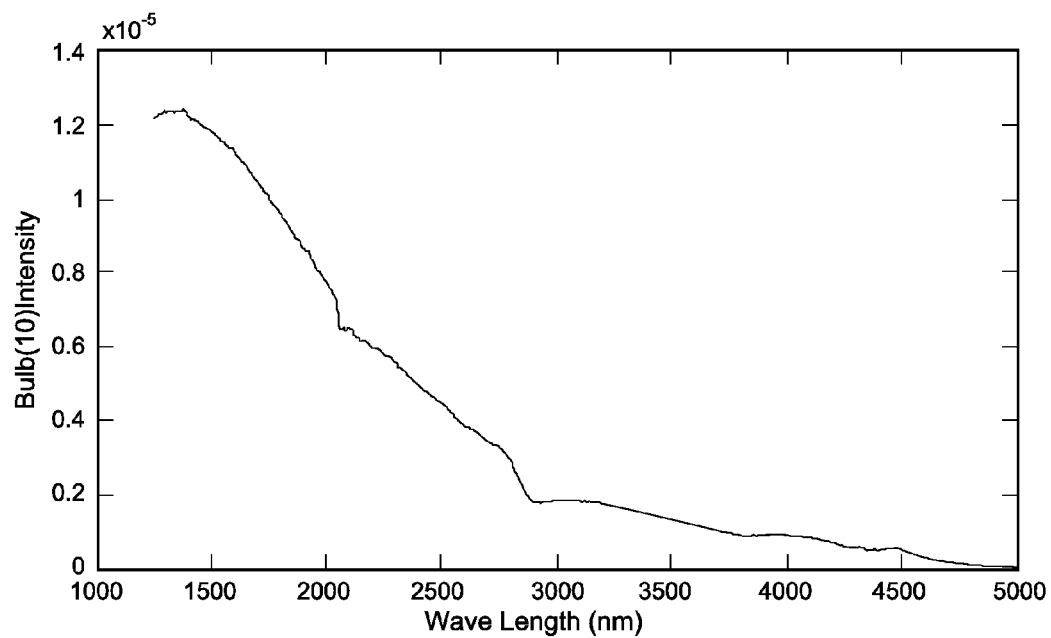
Figure 2C:
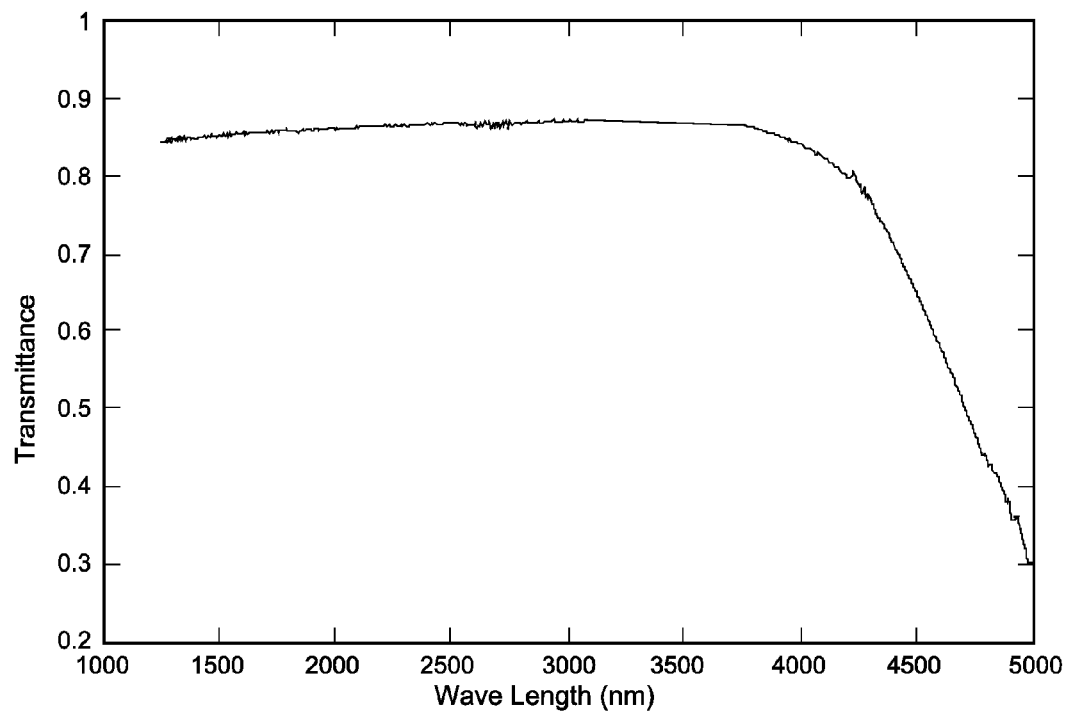
Figure 2D:
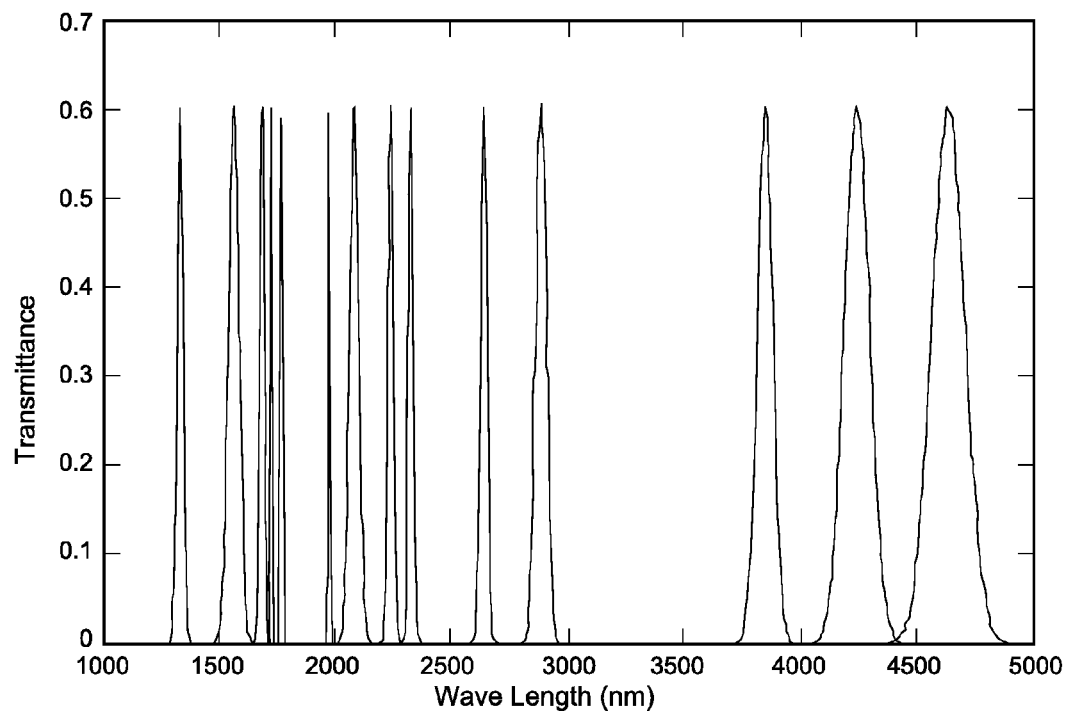
Figure 2E:
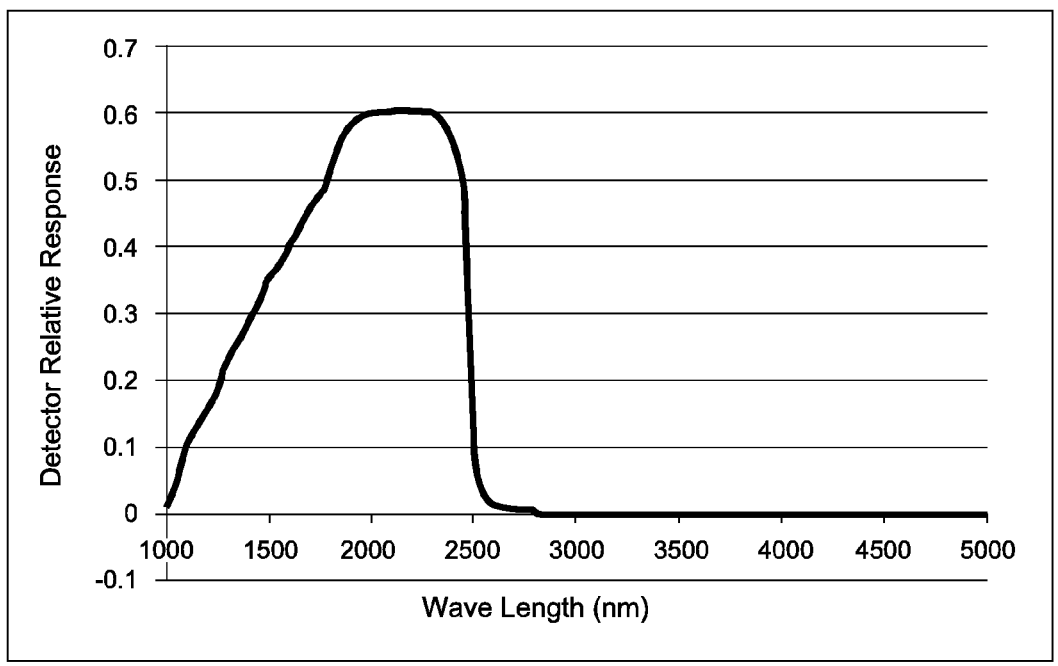
Figure 2F:
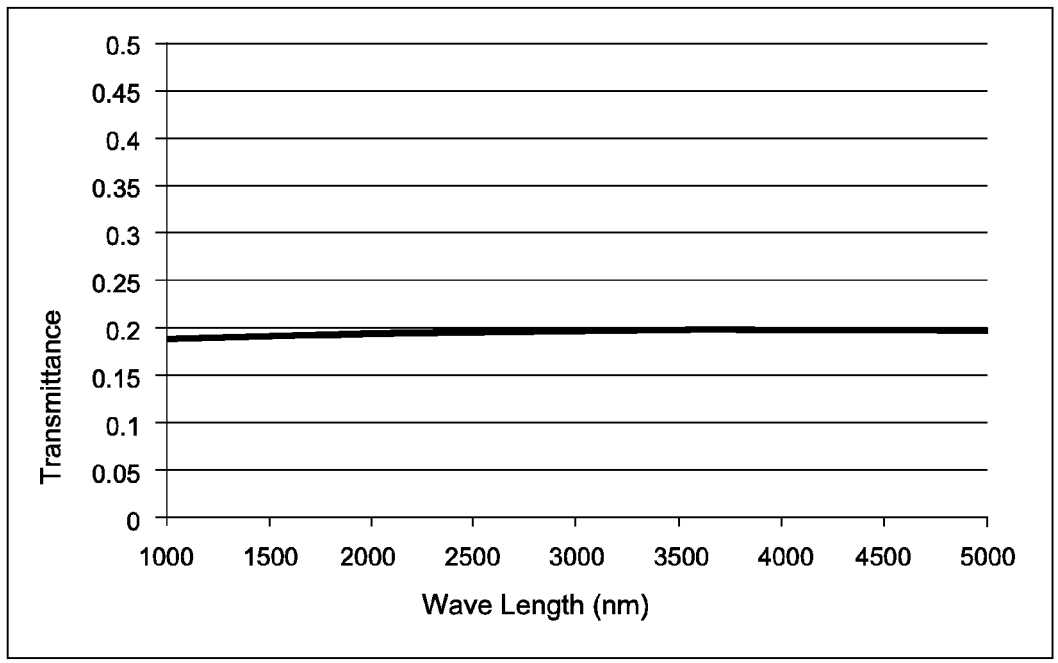
Figure 2G:
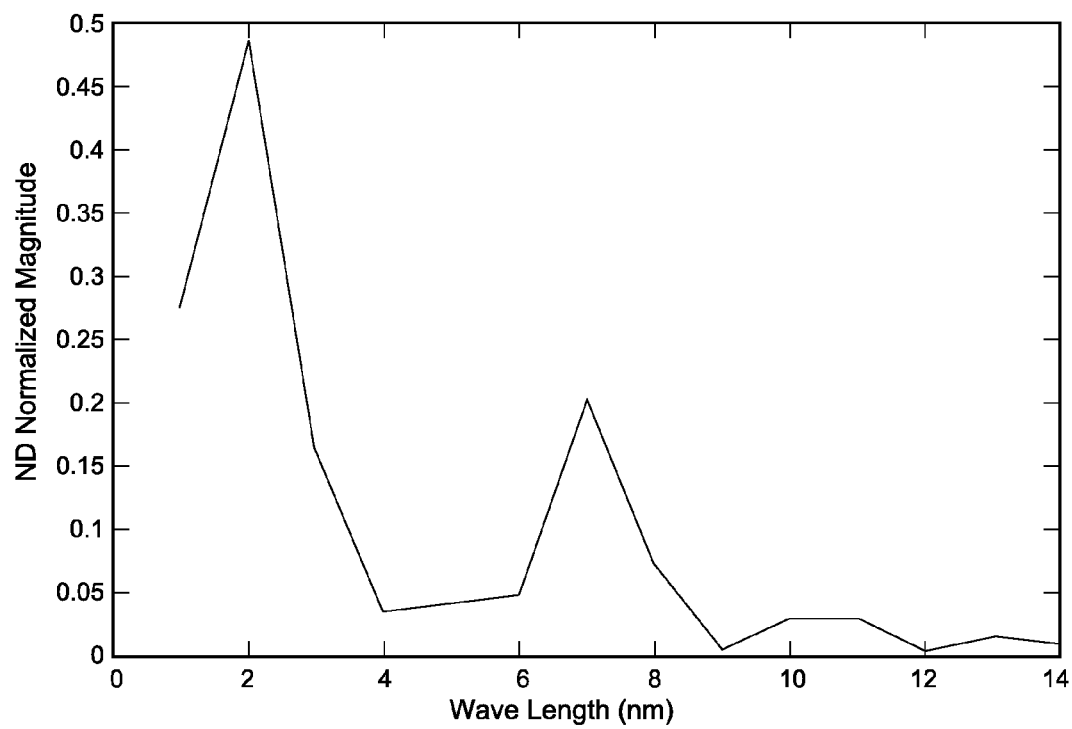
Figure 2H:
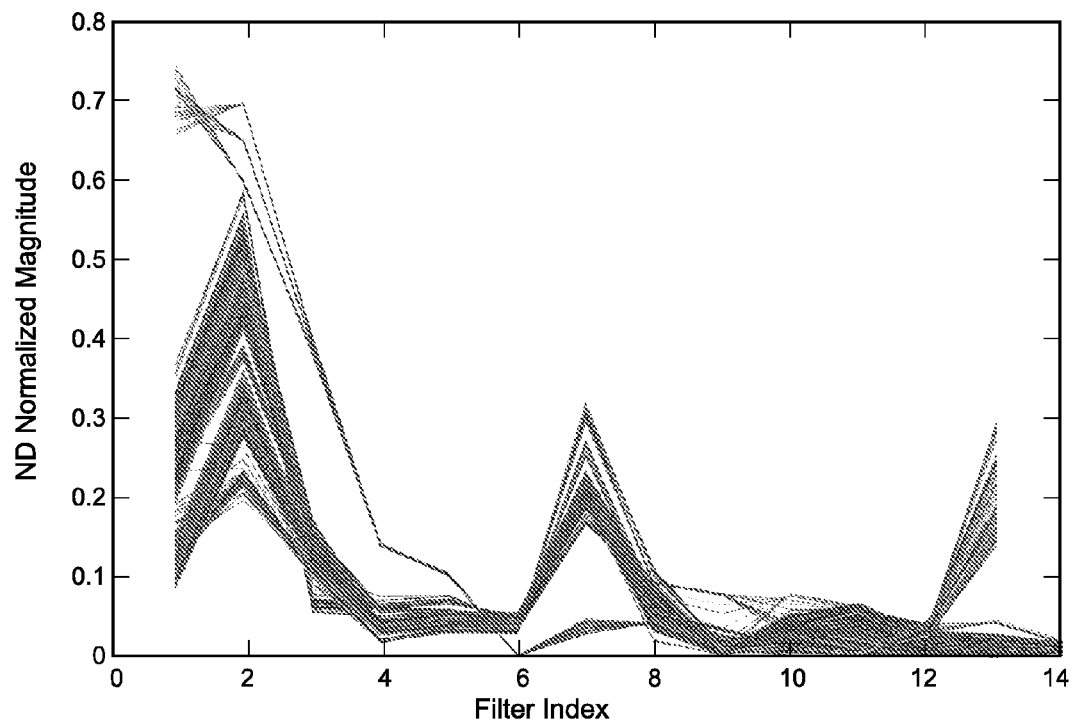

FIGS. 2A-H illustrate example spectra, values, and outputs corresponding to equation (1). FIG. 2A illustrates an example transmittance spectrum, which may correspond with the TrsIR variable and also the output of spectrometer 103 in FIG. 1. FIG. 2B illustrates an example bulb intensity spectrum, which may correspond to variable $I_o$ and may be measured in a laboratory environment based on the bulb of an actual optical tool. In certain embodiments, the bulb intensity spectrum in FIG. 2B may correspond to one of multiple possible bulbs that can be used in an optical tool. FIG. 2C illustrates a sapphire window transmittance of the optical tool, which may correspond to variable SapIR and may also be determined in a laboratory environment. FIG. 2D illustrates example theoretical Gaussian filters used to simulate the actual optical sensor (AOS) response of an optical tool, and may correspond to variable NBF(i). These filter values may be selected based on laboratory experiments and modeling. In certain embodiments of the present disclosure, these filter designs may be altered based on a feedback process that will be described below. FIG. 2E illustrates an optical transducer response function. FIG. 2F illustrates a broad band neutral density filter that can be used to normalize the output of equation (1), and may correspond to variable NDF. The spectra, values, and filter types shown in FIG. 2A-F are not meant to be limiting FIG. 2G shows an example CPOS response that is solved for using equation (1) with the variable values shown in FIGS. 2A-F. The CPOS response for each channel is proportional to that of the transmission spectrum in FIG. 2A for the corresponding wavelength range. In other words, for wavelength regions where the fluid in FIG. 2A is more transmissive to electromagnetic radiation, the CPOS response for that corresponding channel is high. Notably, as can be seen in FIG. 2H, the CPOS response for the abstract optical tool can be calculated for every transmittance spectrum within a database, such as database 101 in FIG. 1. As can be seen in FIG. 1, the saved spectra 107 may be retrieved from the database, and a CPOS response can be calculated for each. All of the CPOS responses may then be stored in the database 101, increasing the datapoints within the database 101. This may help with model generation, as will be described below.

In addition to populating the database 101 with the CPOS responses from the optical tool calculation 105, the database 101 may also be populated with AOS responses from optical tools, which have been standardized such that they correspond to the CPOS responses generated by the optical tool calculation 105. Advantageously, when a sample 108 is not available in a laboratory to run through spectrometer 103, the database 101 may still be populated with the additional data corresponding to the sample by applying a standardization algorithm 111 to the AOS response 110 of the optical tool 109. As will be described below with respect to FIG. 6, the standardization algorithm 111 may correlate the AOS response 110 of the optical tool 109 to a sample fluid 108 with the (calculated or predicted) pseudo optical sensor response of an abstract optical tool to the same sample fluid 108. Accordingly, the output of the standardization algorithm 111, standardized actual optical sensor (SAOS) response 112, may be indistinguishable from the (calculated or predicted) pseudo optical sensor responses stored in the database 111.

In certain embodiments, some or all of the steps and elements described above, including optical tool calculation 105, and some or all of the steps and elements described below, may be implemented in an information handling system. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network computer, a network storage device, or any other suitable device and may vary in size, shape, performance, functionality, and price. The information handling system may include random access memory (RAM), one or more processing resources such as a central processing unit (CPU) or hardware or software control logic, read-only memory (ROM), and/or other types of nonvolatile memory. The processing resources may include other processors, such as graphical processing units (GPU). Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Figure 3A:
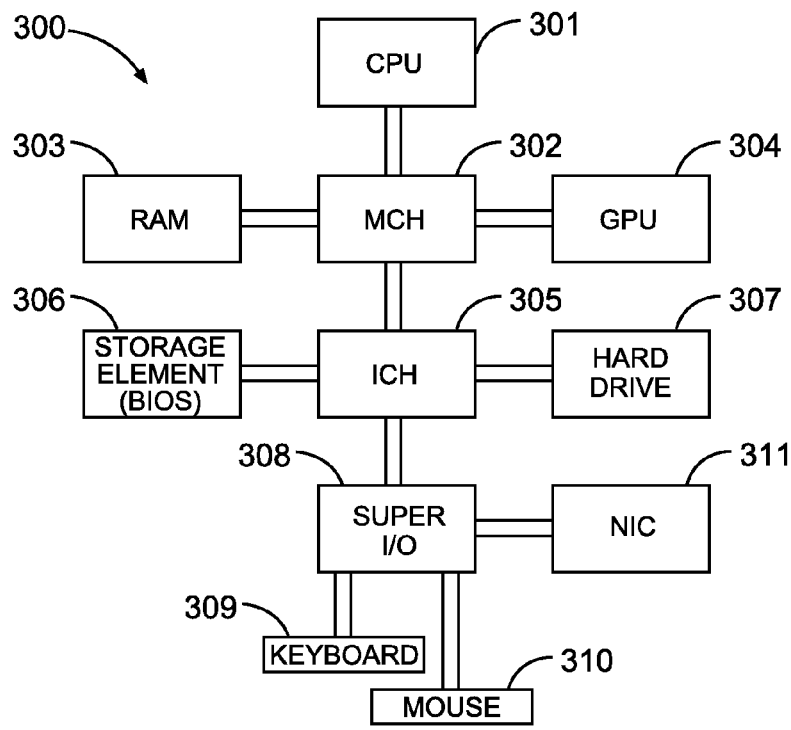
FIG. 3A illustrates an example information handling system, according to aspects of the present disclosure.

Shown in FIG. 3a is a block diagram of an example information handling system 300. A processor or CPU 301 of the information handling system 300 may be communicatively coupled to a memory controller hub or north bridge 302. The memory controller hub 302 may be coupled to RAM 303 and a graphics processing unit 304. Memory controller hub 302 may also be coupled to an I/O controller hub or south bridge 305. I/O hub 305 may be coupled to storage elements of the computer system, including a storage element 306, which may comprise a flash ROM that includes a basic input/output system (BIOS) of the computer system. I/O hub 305 is also coupled to the hard drive 307 of the computer system. The hard drive 307 may be characterized as a tangible computer readable medium that contains a set of instructions that, when executed by the processor 301, causes the information handling system 300 to perform a pre-determined set of operations. For example, according to certain embodiments of the present disclosure, and as will be discussed below, the hard drive 307 may contain instructions that when executed cause the CPU 301 to retrieve certain variable values and determine a solution to equation (1). In certain embodiments, the hard drive 307 may also contain instructions that cause the processor to generate optical fluid ID and optical sensor response models, as will be described below.

In certain embodiments, I/O hub 305 may also be coupled to a super I/O chip 308, which is itself coupled to several of the I/O ports of the computer system, including keyboard 309, mouse 310, and one or more parallel ports. The super I/O chip 308 may further be coupled to a network interface card (NIC) 311. The information handling system 300 may receive various measurements over the NIC 311, for processing or storage on a local storage device, such as hard drive 307. In certain embodiments, the information handling system may communicate with a database, such as database 101, through the NIC 311. The information handling system may then retrieve data from the database, and perform computations on the data using algorithms stored locally within hard drive 307.

Figure 4:
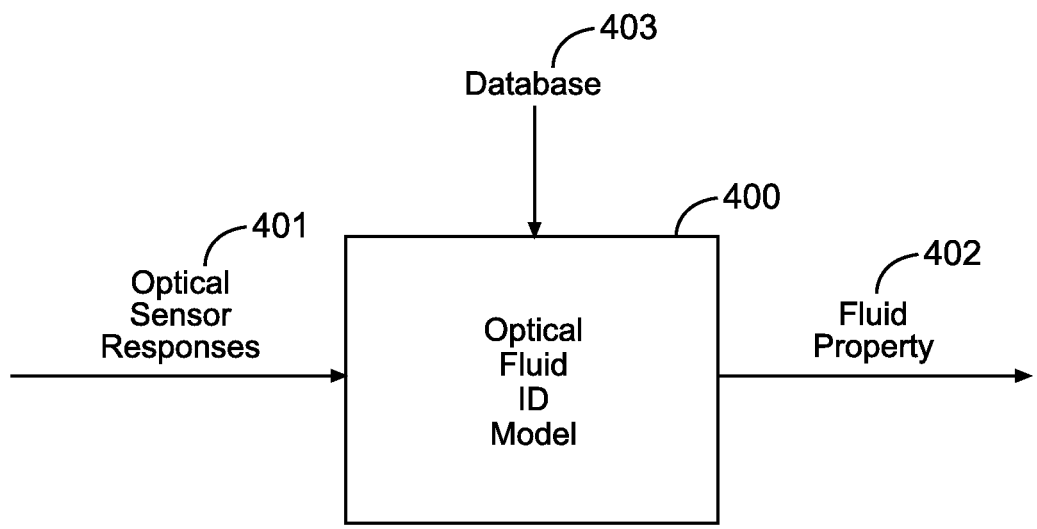
FIG. 4 illustrates an example optical fluid ID prediction model, according to aspects of the present disclosure.

According to aspects of the present disclosure, data stored in a database, such as database 101, may be used to generate an optical fluid ID prediction model 400, shown in FIG. 4. The database 101 may correlate fluid properties with CPOS responses. The optical fluid ID prediction model 400, in contrast, may receive as an input an optical sensor response 401 and output at least one predicted fluid property 402. In certain embodiments, the optical sensor response input 401 may comprise a CPOS response from an abstract optical tool or a SAOS response from an optical tool. Additionally, the optical sensor response input 401 may further comprise a PPOS response, generated from an optical sensor response model, as will be described below with respect to FIG. 5. Notably, each of the CPOS response, the PPOS response, and the SAOS response may have a similar format and be generally indistinguishable with respect to the model 400. By accepting inputs from different sources, the optical fluid ID model 400 may have greater flexibility than typical calibration models used in the art.

Figure 5:
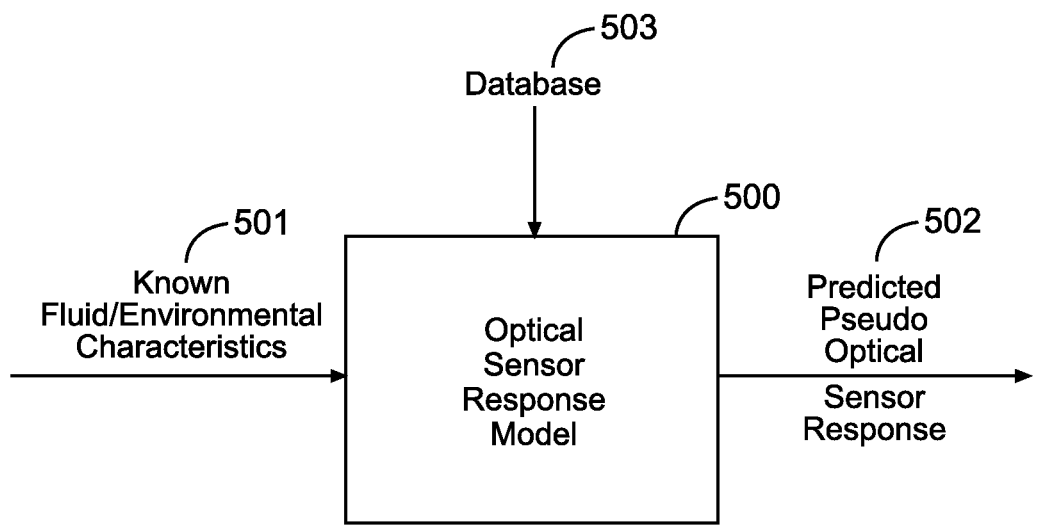
FIG. 5 illustrates an example optical sensor response model, according to aspects of the present disclosure.

FIG. 5 illustrates a second model, optical sensor response model 500, that may be generated from a database 503. Unlike the optical fluid ID model 400, the optical sensor response model 500 may receive as an input a known/measured fluid/environmental characteristic 501 and may output a PPOS response 502 of an abstract optical tool to a sample fluid with a known/measured fluid/environmental characteristic 501. The known/measured fluid/environmental characteristic 501 may include, for example, chemical concentrations of the fluids, fluid densities, etc. The PPOS response 502 may be similar to the CPOS response of the abstract tool described in FIG. 1, except that the PPOS response 502 is generated using model 500, instead of being calculated directly from laboratory measurements of abstract optical tool measurements.

Figure 3B:
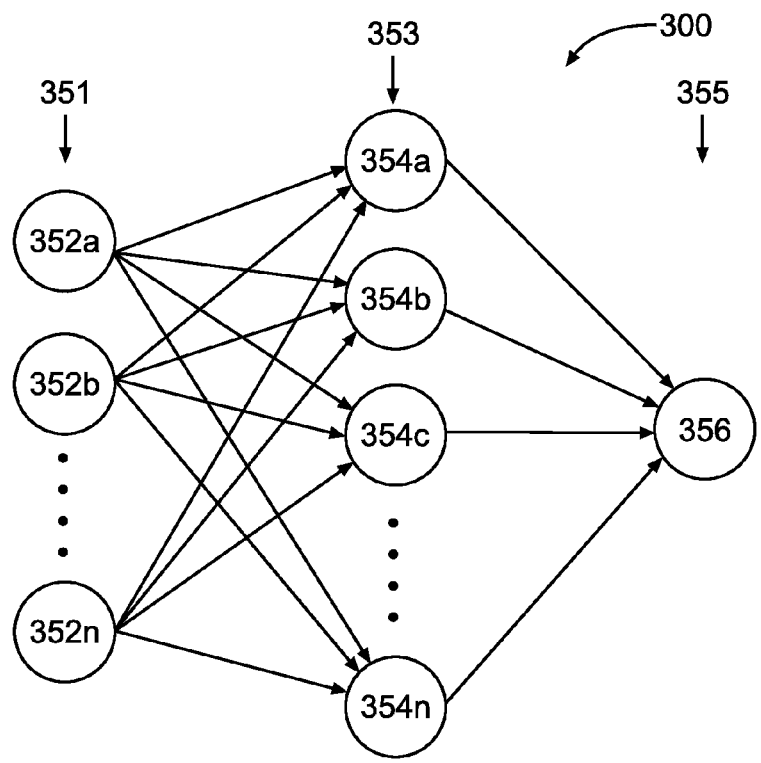
FIG. 3B illustrates an example neural network, according to aspects of the present disclosure.

In certain embodiments, the optical sensor response model 500 may comprise a neural network that is trained using a database, such as database 101, although other linear and non-linear models are possible. One example neural network 350 is illustrated in FIG. 3b. As will be appreciated by one of ordinary skill in the art in view of this disclosure, a neural network 350 may comprise a plurality of neurons that may be physically constructed or simulated by an information handling system. For example, the neurons can be modeled using a processing element and memory in a single computer, or alternatively, some or all of the neurons may be implemented on separate computers, each connected to a network. The neural network 350 may be trained using database 101 to output a PPOS response for an abstract optical tool with a given configuration, which may be accounted for based on CPOS responses stored in the database.

As can be seen, the neural network 350 may include parallel connections between processing elements 352a-n, 354a-n, and 356, which may also be referred to as neurons. In certain embodiments, each neuron receives input signals, and based on an internal weighting system, produces a single output signal. The neurons may be organized into different layers. For example, in FIG. 3a, the neural network 350 includes an input layer 351 comprising neurons 352-n, one or more hidden layers 353 comprising neurons 354a-n, and an output layer 354 comprising neuron 356. As can be seen, the number of neurons in each layer may vary depending on the amount of input variables and the number of values to be output by the neural network 350. According to certain embodiments, known or measured fluid and environmental properties may be input to the neural network 350, with each property being input to a different neuron 352a-n in the input layer. The neurons 354a-n of the hidden layer 353 may then each receive a linear combination value from each neuron 352a-n of the input layer 351, calculate a neuron output with a user-defined transfer function, and feed the signal forward to a neuron 356 at the output layer 353, which generates an output signal or value. The neural network 350 may be trained by applying fluid properties stored in the database to the input layer neurons, and altering the internal weightings of the neurons such that the signal at the output layer 355 matches a CPOS response corresponding to the input fluid properties. Once the neural network 350 is trained, it may be used to determine PPOS responses of an abstract optical tool to sample fluids without the sample fluids being tested in a laboratory environment. For example, the known or measured fluid and environmental property values may be retrieved from downhole testing equipment in a drilling operation and input to the neural network 350. The network 350 may then generate a PPOS response that corresponds to a CPOS response determined in a laboratory, but without the sample fluid actually having to be tested in a laboratory environment. Accordingly, these samples may be used to validate the models when the fluid samples are limited, as will be described below, but also may be used to populate the database with additional data points when the fluid samples are not available in a laboratory environment.

Figure 6:
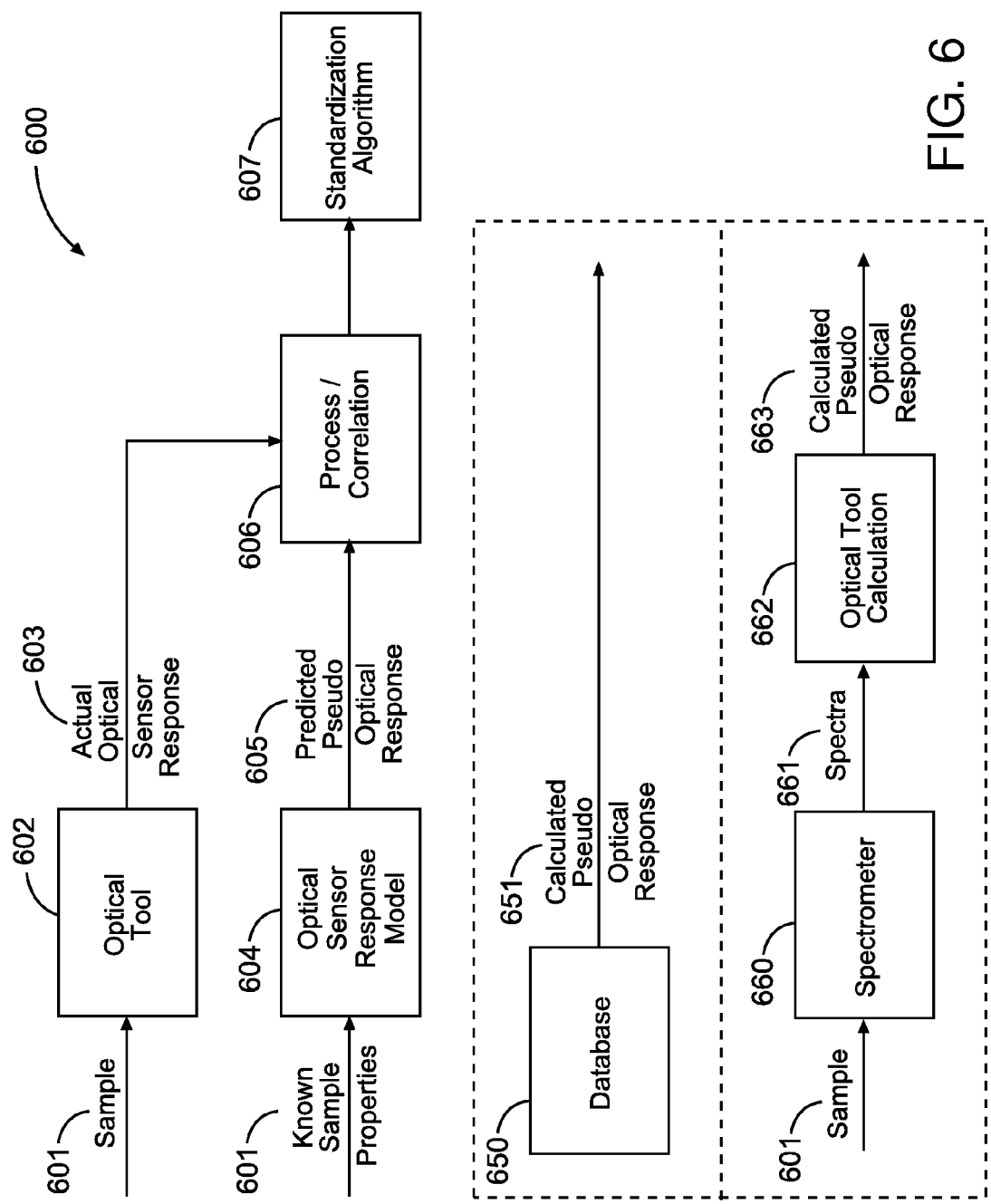
FIG. 6 illustrates an example method for generating a standardization algorithm, according to aspects of the present disclosure.

FIG. 6 illustrates an example flow diagram for generating a standardization algorithm, according to aspects of the present disclosure. As can be seen an optical tool 602 may generate an AOS response 603 to a sample fluid 601. A known/measured property of the sample 601 may be input into an optical sensor response model 604, similar to the one described with respect to FIG. 5, which may output a PPOS response 605 of an abstract optical tool to the sample fluid 601. The AOS response 603 may be correlated with PPOS response 605 at block 606 to generate a standardization algorithm 607. The standardization algorithm 607 could be a multi-input, multi-output neural network that performs multi-channel transformation in a single model. It could also be implemented with multiple models to make one-to-one or several-to-one mapping in each model. The standardization algorithm 607 may receive as an input an AOS response of an optical tool to a sample fluid and output an SAOS response, which may correspond to a PPOS or CPOS response of an abstract optical tool to the sample fluid. Advantageously, using the PPOS response 605 to correlate with the AOS response 603 can allow for calibration/standardization even when a sample fluid is not available for laboratory testing.

Notably, the calibration/standardization is also applicable when a sample fluid is available for laboratory testing and optical sensor calculation. For example, when a similar fluid sample was previously subject to laboratory testing and optical response calculation, the AOS response 603 may be correlated with a CPOS response 651 from a database 650, either alone or in combination with the PPOS response 605. Likewise, when a sample fluid is currently available for testing, spectra 661 for the sample 601 may be generated by the spectrometer 660, and the spectra may be used in an optical tool calculation 662 to generate a CPOS response 663, using tool values that correspond to the optical tool 602, which may be correlated with the AOS response 603.

Figure 7:
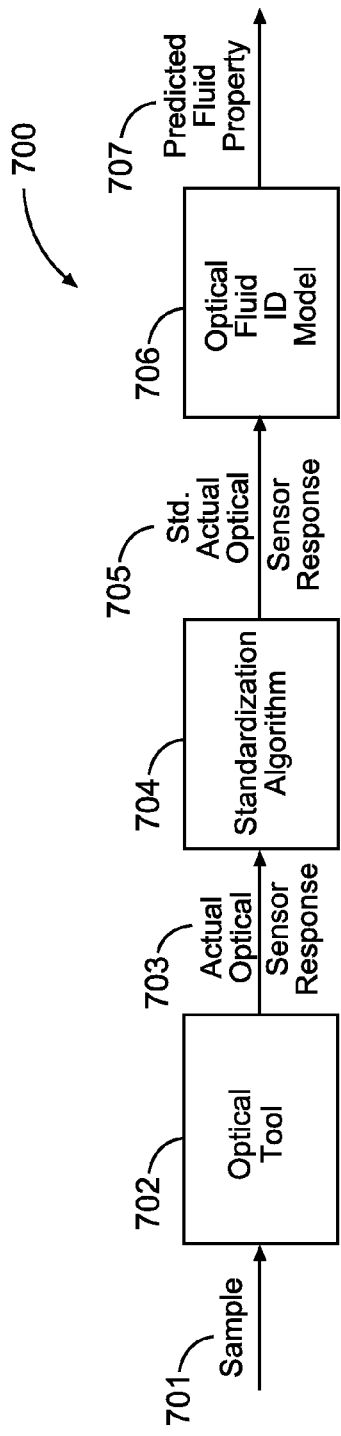
FIG. 7 illustrates an example method, according to aspects of the present disclosure.
Figure 8:
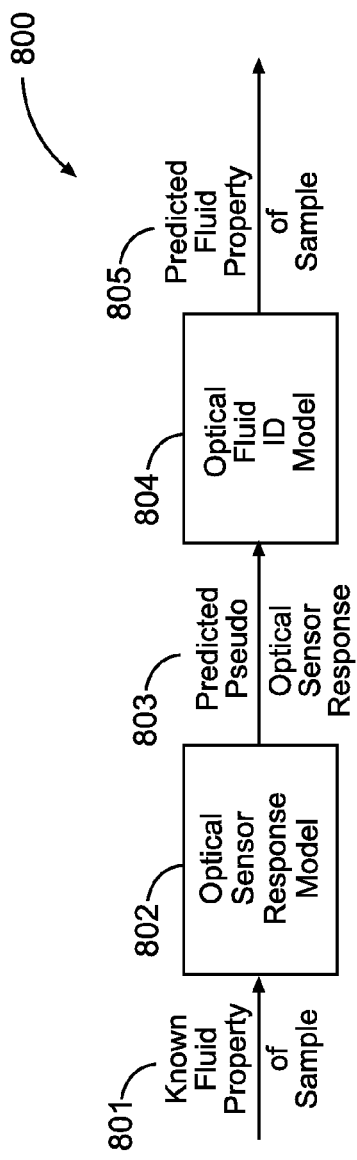
FIG. 8 illustrates an example validation method, according to aspects of the present disclosure.

FIG. 7 illustrates an example method, according to aspects of the present disclosure. The method may include receiving an AOS response 703 of an optical tool 702 to a sample fluid 701. Using a standardization algorithm 704, the AOS response 703 may be transformed to an SAOS response 705, which may correspond to a CPOS or PPOS response of an abstract first optical tool to the sample fluid 701. The SAOS response 705 may then be input an optical fluid ID prediction model 706 to determine at least one fluid property 707 of the sample fluid 701. The optical fluid ID prediction model 706 may be similar to the model described in FIG. 4, and may be generated, at least in part, using a database containing a plurality of CPOS responses of the abstract optical tool to a corresponding plurality of fluid samples. The at least one fluid property 707 may then be used to determine a subterranean formation characteristic, or to alter a downhole operation.

In certain embodiments, the optical sensor response model and optical fluid ID model may be used together to validate the models' efficacy. For example, as can be seen in certain embodiments, a known fluid property of a sample fluid 801 may be input into an optical sensor response model 802, which may generate a PPOS response 803 of an abstract tool to the sample fluid. The PPOS response 803 may then be input into an optical fluid ID model 804 which may output a predicted sample fluid property 805 of the sample fluid. In certain embodiments, the known property 801 and the predicted property 805 may be the same, such that the values can be compared. If the predicted value 805 matches the known value 801, the models have been validated. If the predicted value 805 does not match the known value 801, then the models may be recalibrated using various PPOS responses, CPOS responses, and AOS responses. In certain other embodiments, the predicted property 805 may be different from the known property 801, but may correspond to a different known property of the formation, allowing the models to be validated.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the applicant. The indefinite articles "a" or "an," as used in the claims, are defined herein to mean one or more than one of the element that it introduces. Additionally, although the word "transmittance" is in the claims, it should be understood that "transmittance" is used instead of a more general term, for the sake of clarity. Accordingly, within the context of the claims and the equations, "transmittance" means transmittance, absorbance, reflectance, and diffuse reflectance.

What is claimed is:

1. A method for optical fluid identification approximation and calibration, comprising:
    populating a database with a calculated pseudo optical sensor (CPOS) response of a first optical tool to a first sample fluid, and at least one property of the first sample fluid;
    generating a first model using the database, wherein the first model receives as a first model input an optical sensor response to a second sample fluid;
    outputting a predicted fluid property of the second sample fluid based on the first model;

generating a second model using the database, wherein the second model receives as a second model input at least one known fluid property value of the second sample fluid;
outputting a predicted pseudo optical sensor (PPOS) response of the first optical tool to the second sample fluid based on the second model;
calibrating the first optical tool based, at least in part, on the PPOS response; and
performing a downhole operation based on the predicted fluid property.

2. The method of claim 1, further comprising generating a standardization algorithm by calibrating an actual optical sensor (AOS) response of a second optical tool to the second sample fluid with at least one of:
a CPOS response of the first optical tool to the second sample fluid; and
the PPOS response of the first optical tool to the second sample fluid.

3. The method of claim 2, wherein the optical sensor response to the second sample fluid comprises at least one of:
the CPOS response of the first optical tool to the second sample fluid;
a standardized actual optical sensor (SAOS) response of a second optical tool to the second fluid; and
the PPOS response of the first optical tool to the second sample fluid.

4. The method of claim 3, further comprising validating the first model based, at least in part, on the PPOS response of the first optical tool to the second sample fluid.

5. The method of claim 4, wherein validating the first model comprises:
using the PPOS response of the first optical tool to the second sample fluid as an input to the first model;
comparing the predicted fluid property of the second sample fluid generated by the first model with a known fluid property; and
if the predicted fluid property does not match the known fluid property, calibrating the first model using the PPOS response of the first optical tool to the second sample fluid and the CPOS response of the first optical tool to the second sample fluid.

6. The method of claim 1, wherein the CPOS response of a first optical tool is determined using the following equation:

$$OS(i)=(SyS \times FiL(i))/(SyS \times NDF)$$

where OS(i) comprises an optical sensor response; SyS comprises an optical system transmittance function; FiL (i) comprises a plurality of optical filters; and NDF comprises a broad band neutral density filter.

7. The method of claim 1, wherein the second model comprises at least one neural network trained, at least in part, using the database.

8. A method for optical fluid identification approximation and calibration, comprising:
receiving an actual optical sensor (AOS) response of a first optical tool to a first sample fluid;
transforming the AOS response of the first optical tool to a pseudo optical sensor response of a second optical tool to the first sample fluid;
using the pseudo optical sensor response as a first input to a first model to predict at least one fluid property of the first sample fluid, wherein the first model is generated, at least in part, using a database containing a plurality of calculated pseudo optical sensor (CPOS) responses of the second optical tool to a corresponding plurality of fluid samples;
calibrating the first optical tool, wherein calibrating the first optical tool comprises correlating the AOS response of the first optical tool to the first sample fluid with at least one of:
a CPOS response of the second optical tool to the first sample fluid; and
a predicted pseudo optical sensor (PPOS) response of the second optical tool to the first sample fluid, wherein the PPOS response of the second optical tool to the first sample fluid is determined using a second model that is generated, at least in part, using the database;
validating an efficacy of at least one of the first model and the second, wherein the validation comprises:
receiving as a second input to the second model, a known fluid property of the first sample fluid to determine the PPOS response;
receiving, as a third input to the first model, the PPOS response; and
outputting, from the first model, a predicted sample fluid property of the first sample fluid;
performing a downhole operation based on the predicted sample fluid property.

9. The method of claim 8, wherein the plurality of CPOS responses of the second optical tool using the following equation:

$$OS(i)=(SyS \times FiL(i))/(SyS \times NDF)$$

where OS(i) comprises an optical sensor response; SyS comprises an optical system transmittance function; FiL (i) comprises a plurality of optical filters; and NDF comprises a broad band neutral density filter.

10. The method of claim 8, wherein correlating the AOS response of the first optical tool to the first sample fluid comprises a standardization algorithm, wherein the standardization algorithm comprises at least one neural network transformation algorithm.

11. The method of claim 8, wherein the second model comprises at least one neural network transformation algorithm.

12. The method of claim 8, wherein the validating comprises:
comparing the predicted sample fluid property with the known fluid property;
if the predicted sample fluid property does not match the known fluid property, calibrating the first model using the PPOS response of the second optical tool to the second sample fluid and the CPOS response of the second optical tool to the second sample fluid.

13. A system for optical fluid identification approximation and calibration, comprising:
a database, wherein the database contains a plurality of calculated pseudo optical sensor (CPOS) responses of a first optical tool to a corresponding plurality of fluid samples;
a second optical tool; and
an information handling system in communication with the second optical tool, wherein the information handling system comprises a processor and at least one storage device, wherein the at least one storage device contains instructions that, when executed by the processor, cause the processor to:
receive an actual optical sensor (AOS) response of the second optical tool to a first sample fluid;

transform the AOS response of the second optical tool to a pseudo optical sensor response of the first optical tool to the first sample fluid;

use the pseudo optical sensor response as an input to a first model to determine at least one fluid property of the first sample fluid, wherein the first model is generated, at least in part, using the database;

calibrate the second optical tool based on an output of the first model; and perform a downhole operation based on the determined at least one fluid property.

14. The system of claim 13, wherein the instructions further cause the processor to validate the first model using a second model generated using the database.

15. The system of claim 14, wherein the second model receives as an input at least one known fluid property value of a second sample fluid and outputs a predicted pseudo optical sensor (PPOS) response of the first optical tool to the second sample fluid.

16. The system of claim 13, wherein the plurality of CPOS response are determined by solving equation the following equation:

$$OS(i)=(SyS \times FiL(i))/(SyS \times NDF)$$

where $OS(i)$ comprises an optical sensor response; $SyS$ comprises an optical system transmittance function; $FiL(i)$ comprises a plurality of optical filters; and $NDF$ comprises a broad band neutral density filter.

* * * * *